US 6,547,774 B2

(12) United States Patent  
Ono et al.

(10) Patent No.: US 6,547,774 B2  
(45) Date of Patent: *Apr. 15, 2003

(54) DISPOSABLE ABSORBENT UNDERGARMENT

(75) Inventors: Yoshio Ono, Ehime-ken (JP); Yoshihisa Fujioka, Kagawa-ken (JP); Yoshikazu Takigawa, Kagawa-ken (JP)

(73) Assignee: Uni-Charm Corporation, Ehime-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/709,890

(22) Filed: Sep. 11, 1996

(65) Prior Publication Data

US 2003/0045855 A1 Mar. 6, 2003

(30) Foreign Application Priority Data

Sep. 13, 1995 (JP) ............................... 7-234988

(51) Int. Cl.⁷ ........................... A61F 13/15; A61F 13/20
(52) U.S. Cl. ........................... 604/385.29; 604/385.03; 604/385.14; 604/385.25; 604/385.13; 604/387; 604/396; 604/398; 604/402
(58) Field of Search .................... 604/385.1, 385.2, 604/386, 387, 389–402, 385.24–385.3; 2/385.16, 385.17, 385.03, 385.14, 401–408, 920

(56) References Cited

U.S. PATENT DOCUMENTS

| | | | | |
|---|---|---|---|---|
| 1,112,162 A | * | 9/1914 | Rovira | 604/398 |
| 1,144,253 A | * | 6/1915 | Rubel | 604/402 |
| 1,288,848 A | * | 12/1918 | Dudley | 604/396 |
| 2,030,306 A | * | 2/1936 | Lain | 604/402 |
| 2,088,800 A | * | 8/1937 | Malouf | 604/397 |
| 2,134,925 A | * | 11/1938 | Nichols | 604/401 |
| 2,165,561 A | * | 7/1939 | Marcus | 2/406 |
| 2,246,714 A | * | 6/1941 | Blair | 2/407 |
| 2,401,457 A | * | 6/1946 | Bryant | 604/397 |
| 2,490,137 A | * | 12/1949 | Keller | 2/401 |
| 2,492,620 A | | 12/1949 | Cohen | |
| 2,523,079 A | * | 9/1950 | Walter et al. | 604/401 |

(List continued on next page.)

FOREIGN PATENT DOCUMENTS

| | | | | |
|---|---|---|---|---|
| AU | 208949 | * | 8/1955 | 604/402 |
| CH | 0127502 | * | 1/1929 | 604/396 |
| CH | 304690 | * | 4/1955 | 604/401 |
| CH | 310231 | * | 12/1955 | 2/406 |
| CH | 324889 | * | 11/1957 | 604/394 |
| DE | 257005 | * | 2/1913 | 604/396 |
| DE | 839244 | * | 5/1952 | 604/392 |
| FR | 1276791 | * | 10/1961 | 604/396 |
| GB | 436869 | * | 10/1935 | 604/394 |
| GB | 904058 | * | 8/1962 | 2/406 |
| GB | 2284741 | | 6/1995 | |
| NL | 46259 | * | 2/1939 | 2/406 |

*Primary Examiner*—Dennis Ruhl  
*Assistant Examiner*—K. M. Reichle  
(74) *Attorney, Agent, or Firm*—Lowe Hauptman Gilman & Berner, LLP

(57) ABSTRACT

An absorbent disposable undergarment includes an outer garment, such as pants, in combination with a detachable absorbent pad attached inside thereof. First suspending flaps hang down from an inner side of a stretchable waist-opening peripheral edge of the pants toward a crotch section of the pants. The first suspending flaps are provided with first fastener elements that are disposed remote from the waist opening of the pants. Second suspending flaps extend upwardly from longitudinally opposite ends of the absorbent pad. The second suspending flaps are provided with second fastener elements, that are adapted to mate with the first fastener elements, and are disposed remote from the core of the pad. These second fasteners are releasably engaged with the first fasteners.

16 Claims, 3 Drawing Sheets

U.S. PATENT DOCUMENTS

| | | | |
|---|---|---|---|
| 2,596,127 A | * 5/1952 | Carmean | 604/396 |
| 2,606,588 A | * 8/1952 | Kennette | 604/399 |
| 2,652,057 A | * 9/1953 | Siegel et al. | 604/394 |
| 2,675,806 A | * 4/1954 | Bram | 604/396 |
| 2,678,648 A | * 5/1954 | Woskin | 604/396 |
| 2,703,085 A | * 3/1955 | Schmidt | 604/398 |
| 2,731,014 A | * 1/1956 | Hollingsworth | 604/402 |
| 2,793,642 A | 5/1957 | Andruhovici | |
| 2,859,752 A | * 11/1958 | Haber | 604/396 |
| 2,954,770 A | * 10/1960 | Roth | 604/396 |
| 3,035,576 A | * 5/1962 | Collier | 604/396 |
| 3,788,323 A | * 1/1974 | Robinson | 604/399 |
| 4,013,816 A | * 3/1977 | Sabee et al. | |
| 4,022,212 A | 5/1977 | Lovison | |
| 4,338,939 A | 7/1982 | Daville | |
| 4,418,123 A | * 11/1983 | Bunnelle et al. | |
| 4,597,760 A | 7/1986 | Buell | |
| 4,671,793 A | * 6/1987 | Hults et al. | 604/394 |
| 4,701,172 A | * 10/1987 | Stevens | 604/385.2 |
| 4,753,648 A | * 6/1988 | Jackson | 604/389 |
| 4,808,176 A | 2/1989 | Kielpikowski | |
| 4,892,598 A | * 1/1990 | Stevens et al. | 604/399 |
| 4,936,840 A | * 6/1990 | Proxmire | 604/385.02 |
| 5,098,419 A | * 3/1992 | Gold | 604/396 |
| 5,108,385 A | * 4/1992 | Snyder | 604/391 |
| 5,389,095 A | 2/1995 | Suzuki et al. | |
| 5,449,353 A | * 9/1995 | Watanabe et al. | 604/385.2 |
| 6,061,839 A | * 5/2000 | Smolik | 604/385.03 |
| 6,364,863 B1 | * 4/2002 | Yamamoto et al. | 604/385.27 |

* cited by examiner

DISPOSABLE ABSORBENT UNDERGARMENT

BACKGROUND OF THE INVENTION

The present invention relates to disposable absorbent undergarments and, more particularly, to undergarments of a pants type, such as disposable diapers, training pants for babies, incontinence pants, and the like.

U.S. Pat. No. 4,597,760 discloses a body fluid absorbent garment comprising an overgarment and a body fluid absorbent insert adapted to be detachably attached to the overgarment. The body fluid absorbent insert is used as a disposable diaper or reusable diaper. The insert comprises a liquid-permeable topsheet, a liquid-impermeable backsheet and an absorbent core. The insert is formed with adhesive regions at four corners of its lower surface and is adapted to be releasably fastened to predetermined regions provided on the upper surface of the overgarment.

In the body fluid absorbent undergarment described above circumferential stretchability is provided along a peripheral edge of a waist opening thereof for ease of wearability. However, if the peripheral edge is provided with such circumferential stretchability in the pants type garment having a waist-opening and a pair of leg-openings, it is necessary that a plurality of gathers be formed along the peripheral edge. When the above-mentioned known technique is applied to such an undergarment such that an absorbent pad corresponding to the insert may be detachably attached to the pants corresponding to the overgarment adjacent the waist-opening, the gathers formed along the peripheral edge extending along the waist line obstruct operation of the attachment and the pad can not be attached to the pants over an area required to achieve a reliable attachment. This deficient attachment area will result in an inadequate fastening force and an apprehension that the pad might unintentionally detach from the pants. In addition, the presence of the gathers in the fastening regions will make it difficult to find the fastening regions.

In view of the problem described above, it is a principal object of the invention to provide an undergarment having a circumferentially stretchable waist line peripheral edge which allows the absorbent pad to be easily fastened to the pants without apprehension that the pad might unintentionally detach from the pants.

SUMMARY OF THE INVENTION

The object set forth above is achieved, according to the invention, by an undergarment having a front section, rear section, and crotch section interposed therebetween. The undergarment comprises a pair of leg-openings and a circumferentially stretchable waist-opening. A body fluid absorbent pad, including a topsheet, a backsheet and an absorbent panel disposed therebetween extends longitudinally in and from the crotch section into proximity to the front and rear sections. In accordance with the invention, a pair of first suspending flaps are carried on inner sides of the front and rear sections in circumferentially middle regions thereof. The first suspending flaps hang down from and beyond a peripheral edge region of the waist-opening toward the crotch section and have provided at free ends thereof, first fastening means which are more rigid than the first suspending flaps. The pad has second suspending flaps, formed of at least one of the topsheet and the backsheet or both, extending outward beyond longitudinally opposite ends of the panel. The second suspending flaps are provided with second fastening means which are more rigid than the second suspending flaps and are adapted to be releasably fastened to the first fastening means.

DESCRIPTION OF THE PREFERRED EMBODIMENT

Figure 1:
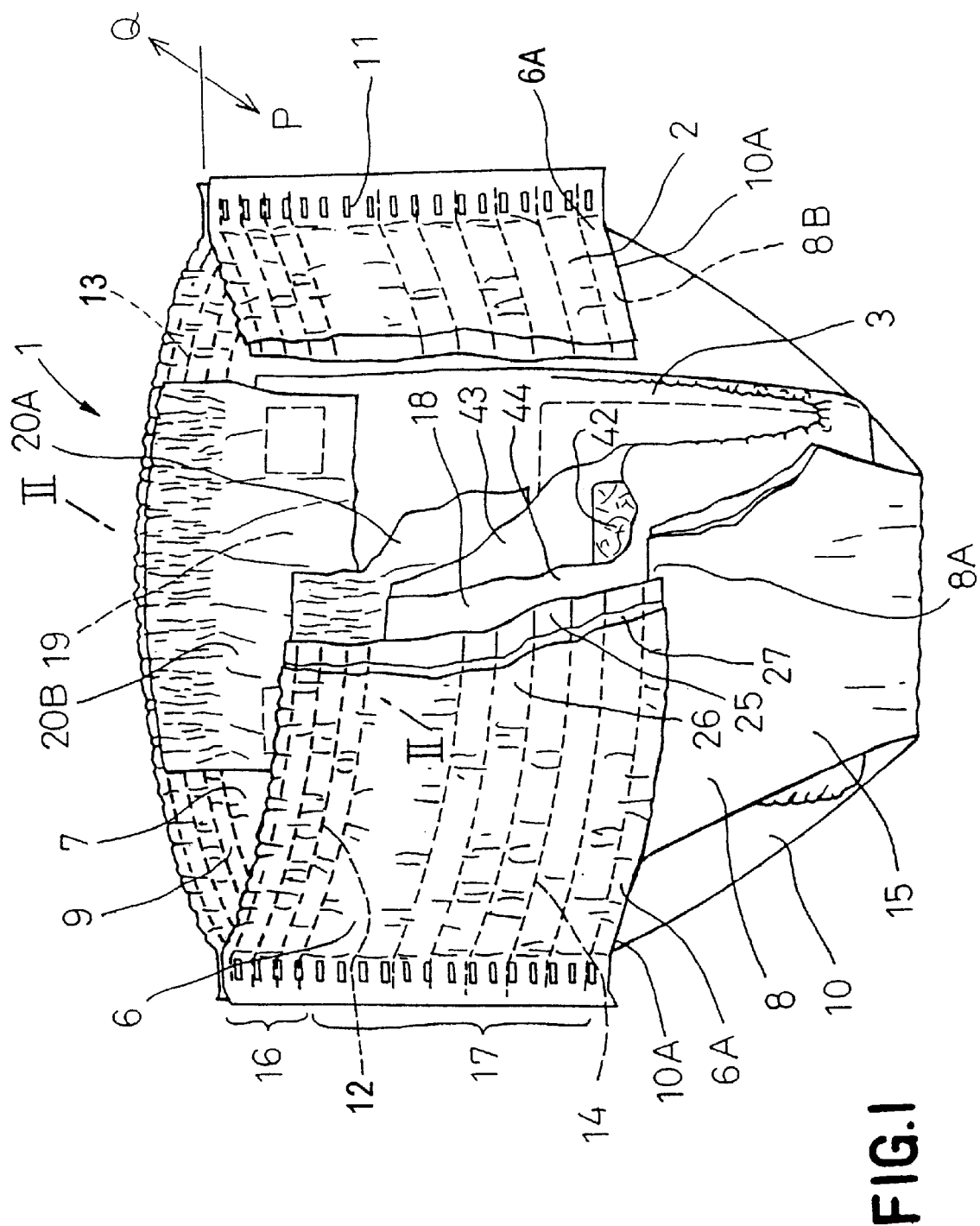
FIG. 1 is a perspective view of incontinence pants partially broken away, of a specific embodiment of the inventive undergarment.

Incontinence pants 1, as depicted in FIG. 1, comprise a main body 2 and an absorbent pad 3 detachably attached to the main body. The main body 2 has a front section 6, a rear section 7, and a crotch section 8 interposed therebetween. Transversely opposite side edges of the front and rear sections 6, 7 are bonded together, for example, along respective heat-seal regions 11 each intermittently extending in their vertical direction so as to form a waist-opening 9. The front and rear sections 6, 7 are provided along respective peripheral edge regions 16 of the waist-opening 9 with first elastic members 12, 13 each comprising a plurality of elastic elements attached thereto in their circumferentially tensioned or stretched condition. Second elastic members 14 are provided along lower waist regions 17 disposed downward of the peripheral edge regions 16. Second elastic members 14, each also comprising a plurality of elastic elements attached thereto in their circumferentially tensioned or stretched condition, are also provided. The crotch section 8 has a sheet member 15, which is stretchable in its longitudinal direction, that is joined at its longitudinally opposite ends 8A, 8B to lower ends 6A, 7A (FIG. 2) of the front and rear sections 6, 7, respectively, immediately above upper ends 10A of the respective leg-openings 10, to form a pair of leg-openings 10. The main body 2 is provided on its inner side with the absorbent pad 3 extending longitudinally in and from the crotch section 8 into a position adjacent to the front and rear sections 6, 7.

Figure 2:
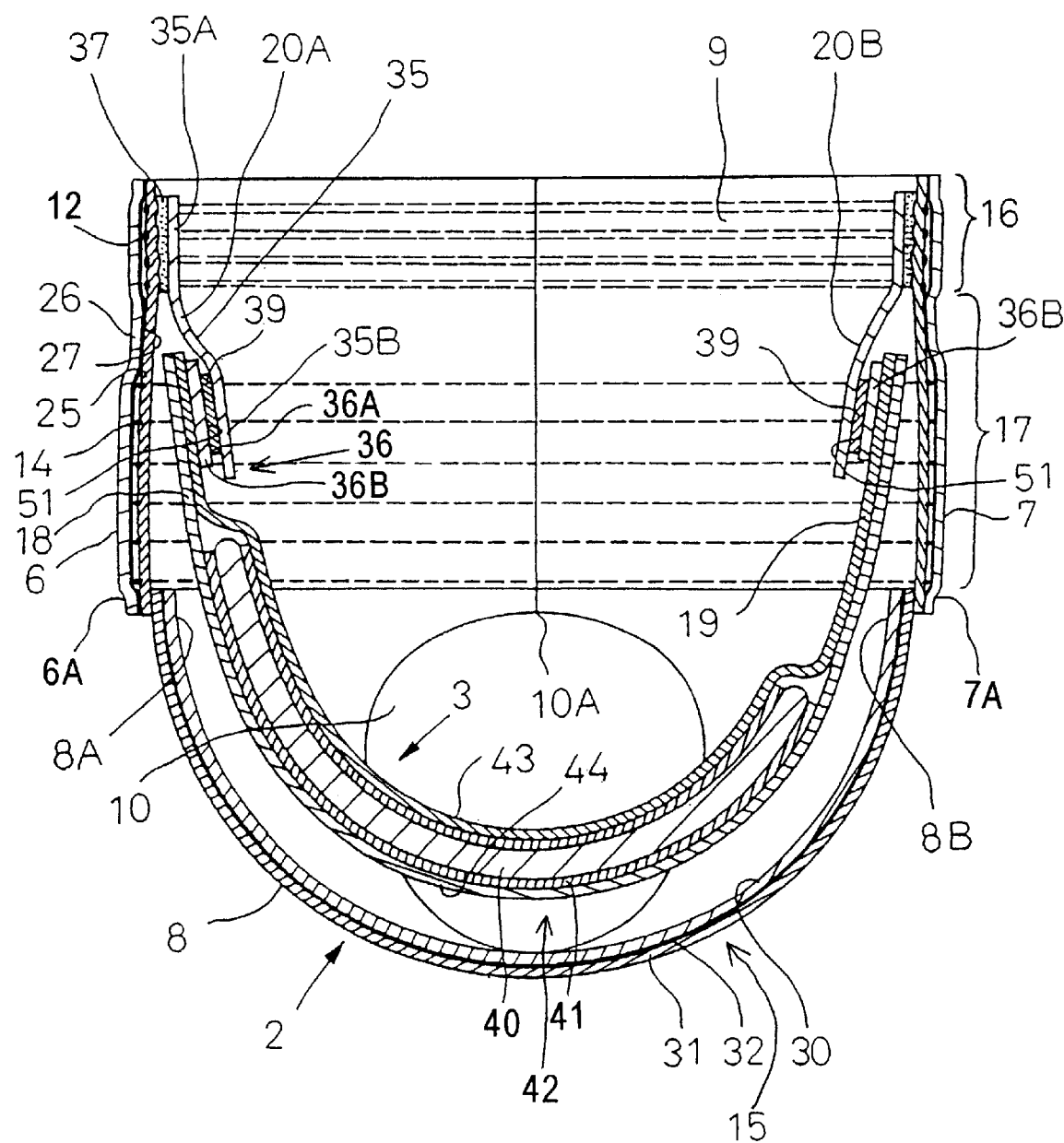
FIG. 2 is a sectional view taken along line II—II in FIG. 1.

FIG. 2 is a sectional view taken along line II—II in FIG. 1. In the main body 2, each of the front and rear sections 6, 7 comprises a topsheet 25 and a backsheet 26, both made of a nonwoven fabric that are intermittently bonded to an air/moisture permeable plastic film 27 disposed therebetween. The first and second elastic members 13, 14 are disposed between the topsheet 25 and the film 27 and are secured to the inner surface of at least one of the topsheet 25 and film 27. The sheet member 15, as a component of the crotch section 8, comprises a topsheet 30 and a backsheet 31, both made of a nonwoven fabric, and an air/moisture-permeable plastic film 32 which is disposed therebetween and stretchable at least in its longitudinal direction. The topsheet 30 and the backsheet 31 are intermittently bonded to the film 32. In the main body 2, the film 27 assures that the front and rear sections 6, 7 have a desired tensile strength and the film 32 assures that the crotch section 8 has a desired tensile strength and stretchability.

The front and rear sections 6, 7 respectively carry on their circumferential middle regions first suspending flaps 20A, 20B. These flaps 20A, 20B are made of a flexible sheet 35 such as a nonwoven fabric, which is soft and agreeable to touch, or cushiony and spongy material such as a plastic film or polyurethane foamed sheet, or a laminate of the nonwoven fabric and spongy material. The first suspending flaps 20A, 20B have their base ends 35A joined by means of hot melt adhesive 37 to the inner surface of the peripheral edge region 16 of the waist-opening 9 and their free ends 35B hanging down toward the crotch section 8 to extend into the lower waist region 17. The free ends 35B are provided on their surface opposed to the inner surface of the main body 2 with first fastening means 39 comprising one component 36A of a pair of mechanical tape fasteners 36 such as loop and hook systems, which is available under the trade name of VELCRO, secured thereto by a suitable means (not shown).

The pad 3 comprises an absorbent panel 42 which comprises, in turn, a compression-molded mixture 40 of fluff pulp fibers and discrete particles of a water insoluble hydrogel with tissue papers 41 covering it. A topsheet 43 and a backsheet 44 cover upper and lower surfaces of the panel 42, respectively. Portions of the topsheet 43 and the backsheet 44 extending outward beyond a peripheral edge of the panel 42 are bonded together. With regard to such extensions, portions extending outward beyond longitudinally opposite ends of the panel 42 form a pair of second suspending flaps 18, 19 interposed between the front and rear sections 6, 7 and the first suspending flaps 20A, 20B, respectively. Surfaces of the second suspending flaps 18, 19 opposed to the first suspending flaps 20A, 20B are provided with second fastening means 51 comprising the other component 36B of the tape fastener 36 are secured thereto by a suitable means (not shown) and operatively associated with the respective components 36A of the tape fastener 36 such that components 36A, 36B may be releasably engaged together. The pad topsheet 43 is made of a liquid-permeable nonwoven fabric or a plastic film. The pad backsheet 44 is preferably made of a liquid-impermeable plastic film. An extremely thin plastic film covered with a nonwoven fabric to improve its strength as well as the touch of the film may also serve as the backsheet 44. A liquid-permeable nonwoven fabric may also be used to form the backsheet 44 so long as the panel 42 has a sufficient moisture holding capability.

Figure 3:
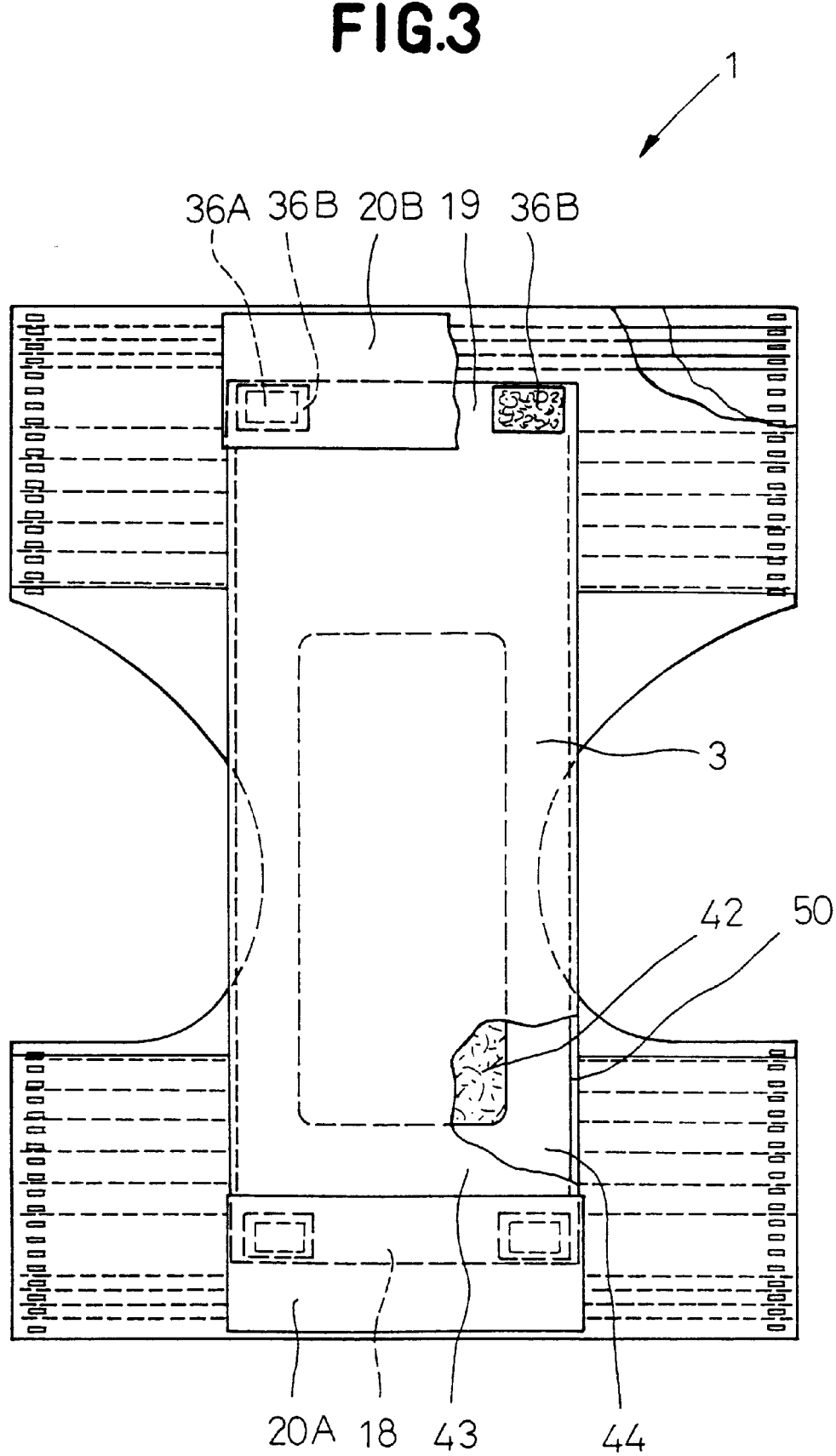
FIG. 3 shows the incontinence pants longitudinally opened out in a plan view with parts broken away.

FIG. 3 is an illustration of pants 1 separated along the heat-seal regions 11 into the front and rear sections 6, 7 and opened out from the position shown by FIG. 1 in the longitudinal direction as indicated by arrows P, Q in a plan view partially broken away. As shown, the pants 1 are opened also in the transverse direction and the gathers formed in the front and rear sections 6, 7 as well as in the crotch section 8 in FIG. 1 disappear as the pants 1 are opened in these two directions. The first suspending flaps 20A, 20B are provided adjacent their transversely opposite ends with component 36A of the tape fastener 36 and the second suspending flaps 18, 19 are provided adjacent their transversely opposite ends with the other component 36B of the tape fastener 36 operatively associated with the component 36A. The pad 3 is provided along its transversely opposite side edges with longitudinally extending elastic members 50, respectively, which are disposed between the topsheet 43 and the backsheet 44 and secured in a tensioned or stretched condition to the inner surface of at least one of these two sheets 43, 44.

In the pants 1 constructed as described above, the flexible sheet 35 for the first suspending flaps 20A, 20B as well as the topsheet 43 and the backsheet 44 of the pad 3 are preferably made of a soft material which is agreeable to touch and does not adversely affect the circumferential stretchability of the front and rear sections 6, 7. For bonding the first suspending flaps 20A, 20B to the main body 2 and for bonding the topsheet 43 and the backsheet 44 together, it is preferred to use soft type adhesive or to arrange intermittent bonding spots in consideration that these components should keep their softness. It is also possible to define the second suspending flaps 18, 19 by one of the topsheet 43 and the backsheet 44 if it is desired to improve the softness in these flaps 18, 19. As a criterion of softness, the first suspending flaps 20A, 20B and the second suspending flaps 18, 19 preferably have a stiffness of less than 150 mm as measured according to JIS P 8143. The presence of the tape fasteners components 36A, 36B increases the rigidities in the first and second fastening means 39, 51 relative to the first and second suspending flaps 20A, 20B, 18, 19 so that the presence of these first and second fastening means 39, 51 can be easily detected by the user's hand as it touches the first and second suspending flaps 20A, 20B, 18, 19 owing to the higher rigidities. If the rigidities of the first and second fastening means 39, 51 themselves are insufficient, such insufficiency can be compensated for by means of the rigidity of the adhesive used to bond the fastener components 36A, 36B to the respective first and second suspending flaps 20A, 20B, 18, 19.

In order to form the first and second fastening means 39, 51, the tape fastener components 36A, 36B may be replaced with pressure-sensitive adhesive. For example, the tape fastener components 36A or 36B may be replaced by pressure-sensitive adhesive tape fastener applied to their underlying member at the corresponding regions to form adhesive fastening regions and the other tape fastener components 36B or 36A may be replaced with relatively thick plastic film sheets bonded to their underlying members at the corresponding regions so that the adhesive fastening regions may be releasably fastened thereto. Instead of these pressure-sensitive adhesive and plastic film sheets, autohesion-type adhesive may be applied to both the first and second fastening means 39, 51 so that the respectively facing pairs of fastening regions coated with this autohesion-type adhesive may be separably bonded together. If the first and second fastening means 39, 51 can not obtain the desired rigidity merely by application of the pressure-sensitive adhesive and bonding of the plastic film sheets, nonwoven fabric or plastic film sheets may be additionally laminated on these fastening means.

In the inventive disposable absorbent undergarment, the first and second suspending flaps 20A, 20B, 18, 19 can be reliably fastened together over adequately large areas without being affected by the gathers formed in the elastic peripheral edge regions 16, since the first and second fastening means 39, 51 respectively provided on the first and second suspending flaps 20A, 20B, 18, 19 are more rigid than the first and second suspending flaps 20A, 20B, 18, 19 themselves, and extend downward beyond the elastic peripheral edge regions 16. Furthermore, such rigidity facilitates detection of the presence of these first and second fastening means 39, 51 and enables the pad to be smoothly mounted or interchanged.

The first fastening regions 39 are provided with their surfaces facing the inner surface of the main body 2 and, in addition, the first suspending flaps 20A, 20B are cushiony, so the first fastening means 39 give the wearer neither a feeling of incompatibility nor uncomfortable irritation, in spite of their relatively high rigidity.

The longitudinally stretchable crotch section 8 contracts in the longitudinal direction and therefore closely contacts the pad 3 against the wearer's crotch to prevent body fluid from leaking therefrom.

What is claimed is:

1. An undergarment assembly comprising:
    an outer undergarment comprising in a longitudinal direction:
        a front section;
        a crotch section, that is stretchable in the longitudinal direction of the undergarment, attached to said front section; and
        a rear section attached to said crotch section opposite to said front section;
    wherein said front and rear sections include a circumferentially stretchable waist band defining an elasticized waist opening;
    wherein said front and rear sections are provided, along respective peripheral edge regions of said waist band, with first elastic members attached thereto in a circumferentially tensioned condition to create said elasticized waist opening by forming gathers in the peripheral edge regions;
    wherein said front and rear sections are further provided along respective other waist regions lying in a region of said waist band that is directed toward said crotch section with second elastic members attached thereto in a circumferentially tensioned condition, said first and second elastic elements being spaced apart and substantially parallel to each other; and
    wherein said crotch section, said front section and said rear section together define a pair of leg openings;
    a body fluid absorbent pad comprising:
        a top sheet;
        a back sheet, and
        disposable, absorbent panel disposed between said top sheet and said back sheet;
    wherein said pad is adapted to be directed toward a wearer of said undergarment and extends longitudinally in said crotch section;
    a pair of first suspending flaps distinct from the first elastic members and having first and second end regions, wherein the first end regions are respectively disposed on inner sides of said front and rear sections, in circumferentially middle regions thereof, and attached to inner portions of said waist band in the peripheral edge regions; and
    wherein the second end regions of said first suspending flaps are directed toward, but do not extend into, said crotch section and are only attached to said undergarment through said first end regions of said first suspending flaps, and thereby dangle loosely;
    first fastening elements, that are spaced from and distinct from said attachments of said first suspending flaps to said waist band, respectively, disposed on said first suspending flaps in a region that is spaced downward from said gathers;
    a pair of second flaps, comprising at least one of said top sheet and said back sheet, that extend, respectively, beyond opposite ends of said absorbent panel and away from said crotch section into the respective front and rear regions and proximity to said first suspending flaps; and
    second fastening elements disposed on said second flaps, respectively, and directed toward said second end regions, respectively, of said first flaps;
    wherein said second fastening elements are adapted to be releasably fastened to said first fastening elements at respective locations that are spaced downwardly from the gathers and remote from said attachments of said first suspending flaps to said waist band.

2. The undergarment as defined in claim 1 wherein said first suspending flaps comprise a soft spongy material.

3. The undergarment of claim 1, wherein said first and second fastening elements are formed of a material that is respectively more rigid than the associated first and second flaps to which said first and second fastening elements are respectively attached.

4. The undergarment assembly of claim 1, wherein the crotch section comprises an air/vapor permeable plastic film that extends substantially along the entire crotch section and is stretchable in the longitudinal direction.

5. The undergarment assembly of claim 1, wherein said second fastening elements are co-elevational with at least one of said second elastic members.

6. The undergarment assembly of claim 1, wherein each of said front and rear sections includes multiple discrete first elastic members attached thereto in the peripheral edge regions.

7. The undergarment assembly of claim 6, wherein all of said multiple discrete first elastic members are coelevational with the first end regions of the first suspending flaps.

8. An undergarment assembly comprising:
    an outer undergarment comprising in a longitudinal direction:
        a front section;
        a discrete crotch section, that is stretchable in the longitudinal direction of the undergarment, attached to said front section; and
        a rear section attached to said crotch section opposite to said front section;
    wherein said front and rear sections include a circumferentially stretchable waist band defining an elasticized waist opening formed with gathers in peripheral edge regions of said waist opening;
    wherein said crotch section, said front section and said rear section together define a pair of leg openings; and
    wherein each of said front, rear and crotch sections comprises an undergarment top sheet and an undergarment back sheet both made of a non-woven fabric and an air/vapor permeable plastic film disposed therebetween, transversely opposite side edges of said front and rear sections being put one upon another and bonded together, longitudinally opposite ends of said discrete crotch section being joined to and overlapping lower ends of said front and rear sections, respectively;
    a body fluid absorbent pad comprising:
        a top sheet;
        a back sheet, and
        a disposable, absorbent panel disposed between said top sheet and said back sheet;
    wherein said pad is adapted to be directed toward a wearer of said undergarment and extends longitudinally in said crotch section;
    a pair of first suspending flaps having first and second end regions, wherein the first end regions are respectively disposed on inner sides of said front and rear sections, in circumferentially middle regions thereof, and attached to inner portions of said waist band in the peripheral edge regions; and
    wherein the second end regions of said first suspending flaps are directed toward, but do not extend into, said crotch section and are only attached to said undergarment through said first end regions of said first suspending flaps, and thereby dangle loosely;
    first fastening elements, that are spaced from and distinct from said attachments of said first suspending flaps to said waist band, respectively, disposed on said first suspending flaps in a region that is spaced downward from said gathers;

a pair of second flaps, comprising at least one of said top sheet and said back sheet, that extend, respectively, beyond opposite ends of said absorbent panel and away from said crotch section into the respective front and rear regions and proximity to said first suspending flaps; and second fastening elements disposed on said second flaps, respectively, and directed toward said second end regions, respectively, of said first flaps;

wherein said second fastening elements are adapted to be releasably fastened to said first fastening elements at respective locations that are spaced downwardly from the gathers and remote from said attachments of said first suspending flaps to said waist band.

9. The undergarment of claim 8, wherein both the topsheet and backsheet are intermittently bonded to the plastic film.

10. The undergarment assembly of claim 8, wherein each of said front and rear sections is provided with a plurality of discrete circumferentially extending first elastic strips attached thereto in the respective peripheral edge regions of said waist opening under a circumferentially tensioned condition, thereby forming said gathers.

11. The undergarment assembly of claim 10, wherein the first elastic strips are sandwiched between the respective undergarment top sheet and back sheet of the front and rear sections.

12. The undergarment assembly of claim 10, wherein each of said front and rear sections further includes a lower waist region immediately adjacent and attached to the crotch section, and a central waist region adjacent to and disposed between the respective peripheral edge region and lower waist region, said lower waist region is provided with a plurality of discrete circumferentially extending second elastic strips spaced from and substantially parallel to the first elastic strips.

13. The undergarment assembly of claim 12, wherein said central waist region is devoid of said first and second elastic strips, the first flaps span over an entire longitudinal length of the central waist region, and said second fastening elements are co-elevational with at least one of said second elastic strips.

14. An undergarment assembly comprising:

an undergarment comprising a longitudinal assembly comprising:
  a front section,
  a rear section, wherein said front and rear sections together define a circumferentially stretchable waist opening;
  wherein each of said front and rear sections are provided, along respective peripheral edge regions of said waist opening, with a plurality of discrete first elastic members attached thereto in a circumferentially tensioned condition to create said waist opening by forming gathers in the peripheral edge regions; and
  a crotch section interposed between said front and rear sections remote from said waist opening, wherein said crotch section and front and rear sections together define a pair of leg openings, said front and rear sections further defining respective lower waist regions that are directed toward said crotch section;
  wherein said front and rear sections are further provided along the respective lower waist regions with second elastic members attached thereto in a circumferentially tensioned condition, said first and second elastic elements being spaced apart and substantially parallel to each other;

a body fluid absorbent pad including a top sheet, a back sheet and absorbent panel disposed therebetween, said panel extending longitudinally in said crotch section, wherein said pad is adapted to be disposed between said crotch section and a wearer of said undergarment;

a pair of discrete first suspending flaps directly attached, respectively, to the peripheral edge regions of said waist opening at inner sides of said front and rear sections in circumferentially middle regions thereof, said first suspending flaps having respective loose dangling ends that are directed away from said respective attachments of said first flaps to said undergarment; wherein said flaps extend from the peripheral edge regions of said waist opening in the direction of said crotch section, and said loose ends are directed toward, but do not extend into, said crotch section;

first fastening elements disposed at the loose ends, respectively, of said first flaps and below and in spaced relation to said gathers and being disposed on surfaces of said first flaps facing a proximate inner surface of said undergarment; wherein said first fastening elements are distinct from said attachments of said first flaps to said front and rear sections, respectively;

second suspending flaps, formed of at least one of said top sheet and said back sheet, extending beyond respective longitudinally opposite ends of said panel from the crotch section into the respective front and rear regions; and second fastening elements supported by said second suspending flaps, respectively, and directed toward said first fastening elements, respectively, and adapted to be releasably fastened to said first fastening elements, wherein places of said attachment of said second fastening elements to said first fastening elements are, respectively, distinct from places of said attachment of said first flaps to said front and rear sections, respectively.

15. The undergarment assembly of claim 14, wherein said first and second fastening elements are formed of a material that is respectively more rigid than the associated first and second flaps to which said first and second fastening elements are respectively attached.

16. The undergarment assembly of claim 14, wherein the first suspending flaps have sufficient length so that the first fastening elements are spaced completely below the respective places of attachment of said first flaps to said waist opening and are separated from the respective places of attachment by regions of said first suspending flaps that are formed without the respective places of attachment or the first fastening elements.

* * * * *